(12) United States Patent
Meriläinen

(10) Patent No.: US 8,992,431 B2
(45) Date of Patent: Mar. 31, 2015

(54) METHOD, APPARATUS AND COMPUTER PROGRAM FOR NON-INVASIVE BLOOD PRESSURE MEASUREMENT

(75) Inventor: Jussi Iisakki Meriläinen, Helsinki (FI)

(73) Assignee: General Electric Company, Schenectady, NY (US)

( * ) Notice: Subject to any disclaimer, the term of this patent is extended or adjusted under 35 U.S.C. 154(b) by 738 days.

(21) Appl. No.: 12/500,159

(22) Filed: Jul. 9, 2009

(65) Prior Publication Data

US 2011/0009756 A1    Jan. 13, 2011

(51) Int. Cl.
| | |
|---|---|
| A61B 5/022 | (2006.01) |
| A61B 5/021 | (2006.01) |
| A61B 5/113 | (2006.01) |
| A61B 5/00 | (2006.01) |

(52) U.S. Cl.
CPC ............ *A61B 5/022* (2013.01); *A61B 5/02116* (2013.01); *A61B 5/113* (2013.01); *A61B 5/7207* (2013.01)
USPC ........................................................ 600/490

(58) Field of Classification Search
CPC ............... A61B 5/022; A61B 5/02108; A61B 5/02116; A61B 5/021; A61B 5/0205; A61B 5/0816
USPC .................................. 600/490–499, 481–485
See application file for complete search history.

(56) References Cited

U.S. PATENT DOCUMENTS

| | | | | |
|---|---|---|---|---|
| 4,889,132 | A * | 12/1989 | Hutcheson et al. | 600/493 |
| 6,358,213 | B1 * | 3/2002 | Friedman et al. | 600/493 |
| 2004/0210143 | A1 * | 10/2004 | Gallant et al. | 600/485 |
| 2005/0187481 | A1 * | 8/2005 | Hatib et al. | 600/485 |
| 2006/0229517 | A1 * | 10/2006 | Lin et al. | 600/490 |
| 2008/0045846 | A1 * | 2/2008 | Friedman et al. | 600/490 |
| 2009/0012411 | A1 * | 1/2009 | Lowe et al. | 600/495 |
| 2010/0249614 | A1 * | 9/2010 | Kolluri et al. | 600/490 |
| 2010/0324428 | A1 * | 12/2010 | Pfeiffer | 600/490 |

FOREIGN PATENT DOCUMENTS

| | | | | | |
|---|---|---|---|---|---|
| WO | WO 2009014420 A1 | * | 1/2009 | ............ | A61B 5/029 |
| WO | WO 2009100927 A1 | * | 8/2009 | ............ | A61B 5/022 |
| WO | WO 2010050798 A1 | * | 5/2010 | ........... | A61B 5/0225 |

OTHER PUBLICATIONS

Michard et al., "Changes in Arterial Pressure during Mechanical Ventilation", Anesthesiology 2005, V. 103, No. 2, pp. 419-428.

* cited by examiner

*Primary Examiner* — Navin Natnithithadha
*Assistant Examiner* — Meredith Weare
(74) *Attorney, Agent, or Firm* — Andrus Intellectual Property Law, LLP

(57) ABSTRACT

A method, apparatus and computer program product are disclosed for non-invasively determining blood pressure related parameters of a subject. A cuff attached to a subject is inflated to a target pressure which is such that normal blood pressure oscillation of the subject appears in an output signal of a pressure sensor monitoring the pressure of the cuff. The output signal of the pressure sensor is acquired for at most a predetermined time period, while the cuff is maintained substantially at the target pressure, thereby to obtain blood pressure waveform data for the subject, and the blood pressure related parameters are derived from the blood pressure waveform data.

14 Claims, 3 Drawing Sheets

METHOD, APPARATUS AND COMPUTER PROGRAM FOR NON-INVASIVE BLOOD PRESSURE MEASUREMENT

BACKGROUND OF THE INVENTION

This disclosure relates generally to non-invasive measurement of blood pressure. The measurement mechanism disclosed may be employed for determining various blood pressure related parameters for a subject that requires efficient hemodynamic monitoring. The subject is typically a mechanically ventilated patient treated in an intensive care unit (ICU), although the measurement may also be applied to spontaneously breathing patients, such as anesthetized patients. Blood pressure related parameters here refer to parameters or variables that may be derived from a blood pressure waveform signal.

Invasive blood pressure measurement is used when continuous tracking of blood pressure is required and when accurate information about the waveform of blood pressure is required. Invasive measurement of blood pressure is also used when an accurate or reliable insight of blood pressure cannot be obtained through non-invasive measurement methods. Invasive blood pressure measurement is therefore useful when brisk changes in the blood pressure are anticipated. Invasive blood pressure monitoring is required for the hemodynamic monitoring of mechanically ventilated patients and in connection with fluid therapy, for example.

Invasive blood pressure measurement is carried out with an intravascular cannulae by placing the needle of the cannulae in an artery. Compared to non-invasive techniques, invasive blood pressure measurements have therefore some drawbacks, which include the risk of infection, thrombosis, and bleeding. Patients with invasive blood pressure monitoring thus require more work and supervision than patients that do not require invasive measurement. Furthermore, non-invasive measurements are simpler to carry out and require less training of the nursing staff. However, the use of non-invasive methods is often not possible, due to the above clear advantages that the invasive methods have in providing accurate and continuous information about the blood pressure waveform.

BRIEF DESCRIPTION OF THE INVENTION

The above-mentioned problems are addressed herein which will be comprehended from the following specification.

In an embodiment, a method for non-invasively determining blood pressure related parameters of a subject comprises inflating a cuff attached to a subject to a target pressure, wherein the target pressure is such that normal blood pressure oscillation of the subject appears in an output signal of a pressure sensor monitoring a pressure of the cuff. The method further comprises acquiring the output signal of the pressure sensor while the cuff is maintained substantially at the target pressure, thereby to obtain blood pressure waveform data for the subject, wherein the acquiring continues at most a predetermined time period, and deriving the blood pressure related parameters from the blood pressure waveform data.

In another embodiment, an apparatus for non-invasively determining blood pressure related parameters of a subject comprises a cuff control unit configured to inflate a cuff attachable to a subject to a target pressure, wherein the target pressure is such that normal blood pressure oscillation of the subject appears in an output signal of a pressure sensor monitoring a pressure of the cuff, and a measurement unit configured to acquire the output signal of the pressure sensor while the cuff is maintained substantially at the target pressure, thereby to obtain blood pressure waveform data for the subject. The apparatus further comprises a control and timer unit configured to enable the measurement unit to acquire the output signal of the pressure sensor for at most a predetermined time period at a time and a parameter determination unit configured to derive the blood pressure related parameters from the blood pressure waveform data.

In a still further embodiment, a computer program product for non-invasively determining blood pressure related parameters of a subject comprises a first program product portion configured to control a cuff control unit to inflate a cuff attachable to a subject to a target pressure, wherein the target pressure is such that normal blood pressure oscillation of the subject appears in an output signal of a pressure sensor monitoring pressure of the cuff, and a second program product portion configured to acquire the output signal of the pressure sensor while the cuff is maintained substantially at the target pressure, thereby to obtain blood pressure waveform data for the subject. The apparatus further comprises a third program product portion configured to enable the second program product portion to acquire the output signal of the pressure sensor for at most a predetermined time period at a time and a fourth program product portion configured to derive the blood pressure related parameters from the blood pressure waveform data.

Various other features, objects, and advantages of the invention will be made apparent to those skilled in the art from the following detailed description and accompanying drawings.

DETAILED DESCRIPTION OF THE INVENTION

Figure 1:
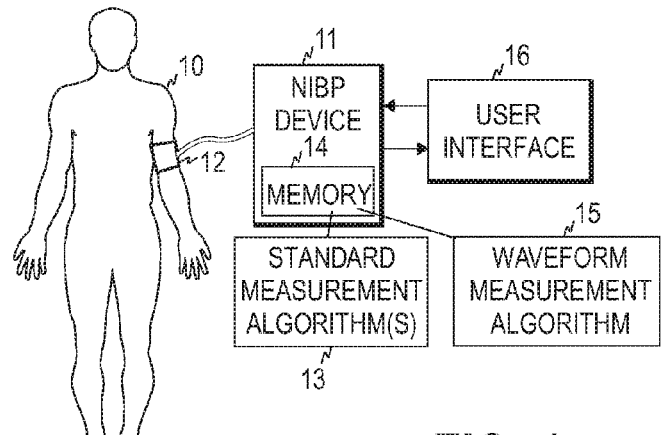
FIG. 1 is a block diagram illustrating one embodiment of an apparatus for non-invasively acquiring blood pressure waveform data from a subject and for deriving blood pressure related parameters/variables from the data.

FIG. 1 illustrates an embodiment of the apparatus for non-invasively determining blood pressure related parameters of a subject 10. The apparatus utilizes a standard non-invasive blood pressure (NIBP) measurement setup in the sense that the apparatus comprises a standard NIBP device 11 provided with a pressurizable cuff 12. The cuff is placed in a normal manner around subject's arm so that the cuff is not touching the chest of the subject. This is to avoid the movement of the chest to disturb the measurement. The standard NIBP device, which may comprise one or more standard algorithms 13 for measuring the blood pressure of the subject, is further provided with a waveform measurement algorithm 15 that utilizes the standard NIBP measurement setup to collect blood pressure waveform data from the subject. The algorithms 13, 15 may be stored in a memory 14 of the NIBP device. The figure further shows the user interface 16 of the NIBP device, through which the user may interact with the device.

It is assumed below that at least two parameters/variables are derived from the blood pressure waveform data collected by the NIBP device of FIG. 1, and that the parameters include systolic pressure variation (SPV) and delta pulse pressure (dPP). SPV and dPP may be used, for example, for optimizing the fluid therapy of a critically ill, mechanically ventilated patient. Fluid therapy, or fluid loading, of a critically ill patient is required to maintain adequate level of cardiac output (CO) and blood flow. Cardiac output is the volume of blood pumped by the heart. Average human CO is around 5 liters/minute. Fluid loading contains a risk of 'overloading' the patient, which may lead to pulmonary edema and/or tissue edema. Thereby, a measure of responsiveness of fluid therapy is required to maintain optimum level of fluid loading. SPV and dPP may be utilized as such measures of responsiveness.

Figure 2:
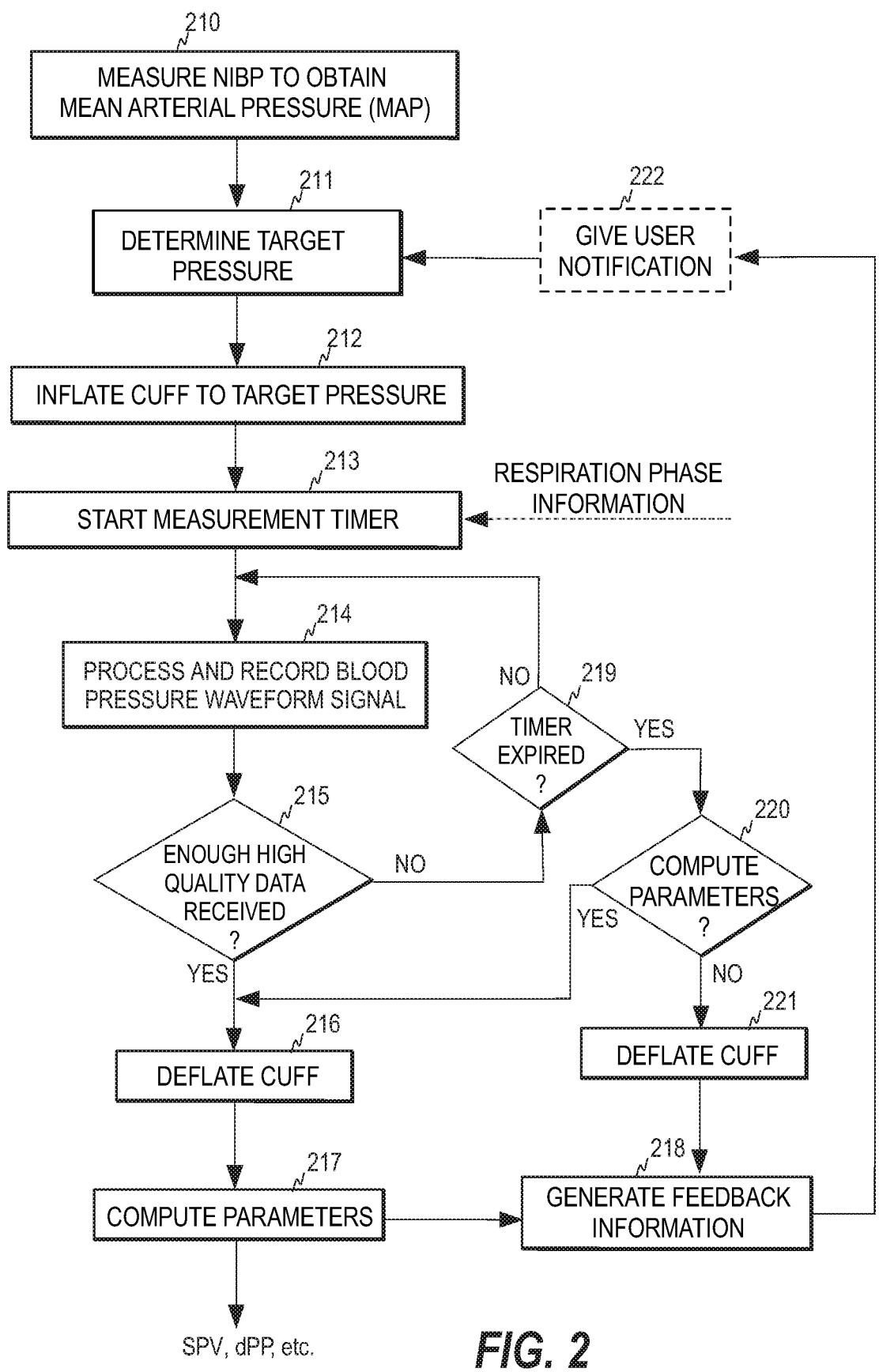
FIG. 2 is a flow diagram illustrating an embodiment of a method for non-invasively acquiring blood pressure waveform data from a subject and for deriving blood pressure related parameters/variables from the data.

FIG. 2 illustrates one embodiment of a method for non-invasively determining SPV and dPP from a subject, using the device of FIG. 1. First, normal NIBP measurement may be carried out at step 210 to obtain a measure indicative of the current blood pressure of the subject. This measure may be, for example, the mean arterial pressure (MAP) of the subject. MAP is defined as the average arterial blood pressure (ABP) during one cardiac cycle. The MAP value is then used at step 211 to determine a target cuff pressure value for the subsequent measurement of the blood pressure waveform. The target cuff pressure is generally such that the normal blood pressure oscillation of the subject appears in the cuff pressure monitored with a pressure sensor of the NIBP device. The initial target cuff pressure may be about 70% of the MAP value, but the initial value may be adjusted for subsequent measurement periods so that the blood pressure waveform data received fulfills predetermined quality criteria. For subsequent measurement periods, the adjustment of the target cuff pressure may be carried out by the feedback information obtained from step 218, as is discussed below.

The cuff 12 attached around the arm of the subject is then inflated to the defined target pressure for the first measurement period (step 212). Once the target pressure is reached, a measurement timer is started (step 213) and the recording of the blood pressure waveform starts (step 214). The start of the measurement timer may be synchronized with the respiration phase of the subject, if such phase information is available. In case of a ventilated subject, the phase information may be obtained from the ventilator as time tags that indicate the significant moments of each respiratory cycle. If the subject breathes spontaneously, the phase information may be obtained directly from a respiration sensor or indirectly from a physiological signal measured from the subject, such as a surface ECG. The target pressure is maintained for the entire measurement period unless adjustment is needed due to low quality of the pressure waveform data received.

At step 214, the pressure waveform data is thus acquired from the cuff pressure signal by recording the output signal of the pressure sensor of the NIBP device, i.e. the output signal represents the waveform signal. Prior to the actual recording of the pressure waveform data, the output signal of the pressure sensor may be subjected to normal signal processing operations, such as amplification, A/D-conversion and removal of noise and/or artefacts. A data quality analysis comprising the detection of respiratory modulation in the pressure curve may also be carried out in step 214. Respiratory modulation here refers to the periodic changes that respiration/breathing causes in the envelope of the blood pressure waveform. The information indicative of the respiration phase, such as the phase of the ventilator cycle, may be used for detecting the respiratory modulation in the pressure signal. In the data quality analysis, the quality of the signal data may be defined in terms of signal amplitude, motion artefacts and/or noise, for example.

If the quality of the signal data is monitored during the recording phase (step 214), the process may also monitor when enough data of acceptable quality is obtained (step 215), thereby to keep the measurement period as short as possible. If the process detects that enough high quality data has been received before the measurement timer expires, the measurement and the timer are stopped, and the cuff is deflated (step 216). The measurement parameters, such as SPV and dPP, are then computed from the said high quality data (step 217).

During the recording phase (step 214), the process also monitors if the measurement timer expires before enough high quality pressure data has been received (step 219). If the measurement timer expires, the process may make a decision on whether or not the parameters are determined (step 220) based on the pressure waveform data collected during the elapsed measurement period. The decision may be made based on the data quality analysis carried out. For example, the parameters may be determined from a shorter time interval comprising high quality data, even though the quality requirement of step 215 is not met. Furthermore, the user of the device may control the operation of step 220 by setting the conditions on which the parameters are determined.

If it is decided in step 220 that the parameters are to be determined, the process depressurizes the cuff and computes the parameters based on the pressure waveform data recorded (steps 216 and 217). In the opposite case (step 220/no), the process simply deflates the cuff (step 221). In each case, however, the process also generates feedback information for the next measurement period, i.e. for the next start of the measurement timer, thereby to enable adjustment of the target pressure in step 211 based on the feedback information. Depending on the content thereof, the feedback information may also induce generation of a user notification in step 222. For example, an informative message may be generated to the user in step 222 if it is decided in step 220 that the parameters cannot be determined due to low quality of the signal.

Based on the feedback information generated after steps 215-217, the process may seek to adjust the target pressure to a minimum value that still yields acceptable signal quality. For example, the feedback information generated in step 218 may in this case indicate to step 211 that the target pressure should be lowered by a given amount, such as 2 percent. If the feedback information is generated after the expiry of the measurement timer and the parameters are determined, a user notification informing that the parameters are based on lower quality pressure data may be produced in step 222. Furthermore, the feedback information may indicate to step 211 that the target pressure should be decreased or increased, depending on the value of current target pressure. If the feedback information is generated after step 221, i.e. if the process was not able to determine the parameters, the feedback information may indicate that the target pressure should be increased or decreased by a given amount, such as 5 percent. Additionally or alternatively, the feedback information may in this case induce a user notification (step 222), informing that the signal was disturbed and the cuff position should be checked. The feedback information may also include information about signal features detected during the recording phase. For example, the feedback information may induce a user notification informing of possible arrhythmias, if the analysis carried out in step 214 implies to such a possibility.

Figure 3:
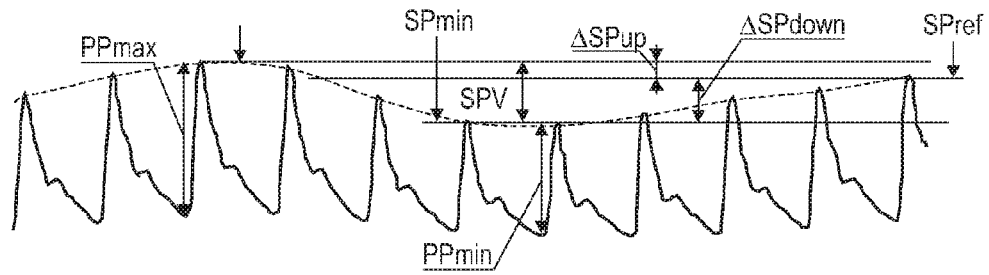
FIG. 3 illustrates a typical blood pressure waveform measured from a subject.

FIG. 3 illustrates an example of the pulse pressure waveform of a ventilated subject during one respiratory cycle. During controlled ventilation the inspiratory pressure limits the preload of the left ventricle, which is aggravated in a hypovolemic patient (hypovolemia=decrease in the volume of the circulating blood). The figure shows the respiratory modulation (dashed curve) and parameters/variables based on which systolic pressure variation and delta pulse pressure may be determined.

Systolic pressure variation (SPV) may be determined from the pressure waveform data by the equation SPV=SPmax−SPmin=(SPmax−SPref)+(SPref−SPmin)=ΔSPup+ΔSPdown, where SPmax and SPmin are, respectively, the maximum and minimum systolic pressure values, and SPref is the mean systolic pressure during a given time period, such one respiratory cycle. The unit of SPV is normally mm/Hg. Pulse pressure is defined as the difference of systolic and diastolic pressures and delta pulse pressure dPP may be determined by the equation dPP=100×(PPmax−PPmin)/((PPmax+PPmin)/2), where PPmax and PPmin are, respectively, the maximum and minimum pulse pressure values during a given time period, such as one respiratory cycle. Delta pulse pressure is measured in percentages.

Stroke volume variation ΔSV may also be determined based on the recorded pressure waveform data by determining the maximum and minimum stroke volumes, i.e. pressure pulse areas, during the systolic phases. The stroke volume variation may be calculated for example as follows:

$$\Delta SV = \frac{SV_{max} + SV_{min}}{2},$$

where SVmax and SVmin are, respectively, the maximum and minimum stroke volumes during a given time period, such as one respiratory cycle.

The parameters/variables determined in step 217 may then employed for evaluating the state of the subject or the treatment given to the subject. SPV and dPP, for example, may be used to determine whether or not cardiac output (CO) is preload dependent. In cardiac physiology, preload is the pressure stretching the ventricle of the heart, after atrial contraction and subsequent passive filling of the ventricle. The cardiac preload dependency is a function of ventricular preload versus stroke volume (=the amount of blood ejected in one cardiac cycle). The value of this information is that it can be used to guide fluid therapy: a preload dependent CO should increase after fluid therapy, whereas administering fluid to a patient whose CO is not preload dependent will probably not increase CO. For example, a doctor can use the SPV and dPP values for making a decision, whether or not the patient should be treated with fluid therapy in order to increase cardiac output or stroke volume. For example, if the dPP value is more than 15%, the patient's heart is preload dependent and therefore fluid therapy should increase the Cardiac Output (Michard et al.: Changes in Arterial Pressure During Mechanical Ventilation, Anesthesiology 2005; 103:419-28). The stroke volume variation may be employed in fluid therapy to predict the change in the stroke volume in response to a given fluid volume. In one embodiment, the above-mentioned components of SPV, ΔSPup and ΔSPdown, may also be determined and displayed to the user, since the said components may be of interest both in case of mechanically ventilated patients and in case of spontaneously breathing anesthetized patients.

The above-described measurement may be repeated when desired. The maximum duration of one recording period, i.e. the measurement period measured by the measurement timer, may be about 1 minute, for example. The measurement may be repeated at regular intervals.

Figure 4:
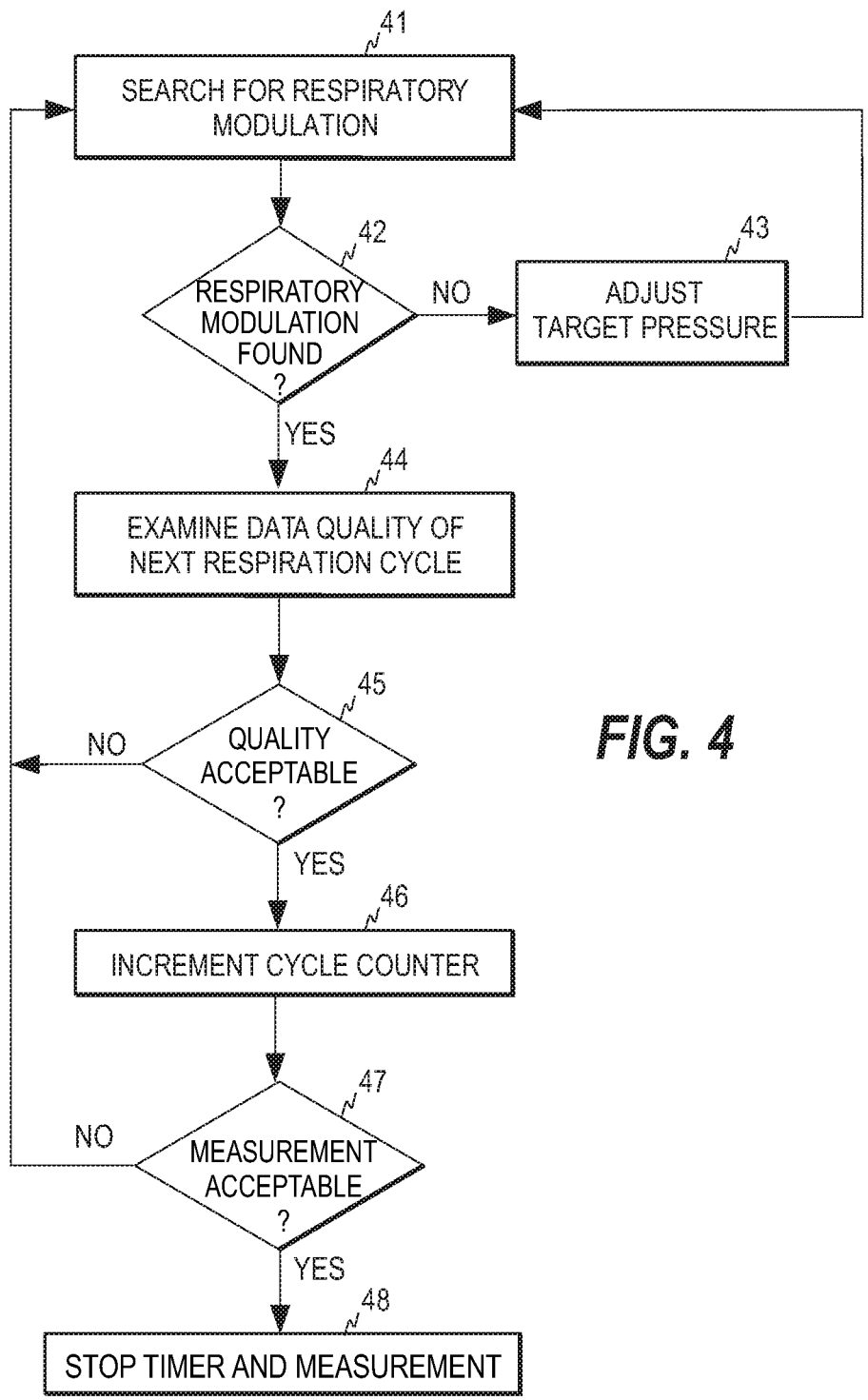
FIG. 4 illustrates an embodiment of the data recording phase of the method.

FIG. 4 illustrates an embodiment of the data quality analysis that may be performed in step 214 of FIG. 2. The purpose of the data quality analysis is to ensure that the parameters are determined based on high quality waveform data. First, the process searches for respiratory modulation appearing in the pulse pressure data received (step 41). If respiratory modulation is detected in step 42, the quality of the pressure waveform data within the first respiratory cycle is examined in step 44. If the respiration modulation is not found in the beginning the data recording, the target pressure may be adjusted (step 43) until the respiratory modulation is detected.

If the quality of the pressure waveform data within the first respiratory cycle is acceptable, the process increments a cycle counter from zero to one (step 46) and jumps to examine the quality of the pressure waveform data within the next respiratory cycle. If the quality is not acceptable, the process skips the incrementing and starts to examine the quality of the pressure waveform data within the next respiratory cycle. In this embodiment, the counter thus indicates, how many respiratory cycles of high quality pressure waveform data has been received. The above operation is continued until it is detected in step 47 that the measurement is acceptable. For example, the process may monitor in step 47 if the number of respiratory cycles with acceptable data quality has reached a predetermined limit. If this occurs before the measurement timer (started at step 23) expires, the timer and thus also the measurement is stopped (step 48). In another embodiment, the cycle counter may be reset to zero if it is detected at step 45 that the quality of the data within the respiratory cycle is not acceptable. That is, the process may require that the high quality data is received in consecutive respiratory cycles. Step 47 may also include a further quality test. For example, it may be required that the lengths of the respiratory cycles with acceptable data do not vary more than a predetermined threshold, such as 10 percent. If it is detected at step 47 that the measurement is not valid, the measurement may continue as long as the measurement timer expires.

The quality analysis performed in step 44 may involve the evaluation of the pressure waveform data in terms of signal amplitude, pulse width, motion artifacts, and/or noise, for example. In one embodiment, the data within a respiratory cycle is regarded as high quality data, i.e. acceptable, if consecutive pulse amplitudes/widths do not vary more than 10 percent from the mean value and if the respiratory cycle contains at least three pulses fulfilling the above criterion.

Figure 5:
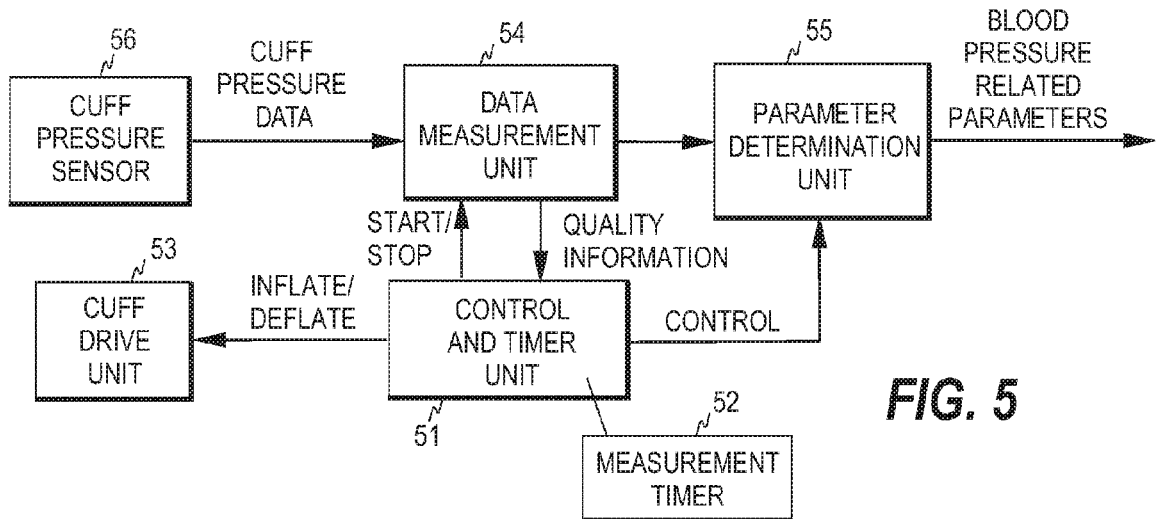
FIG. 5 illustrates the entities of the apparatus for determining blood pressure related parameters.

In terms of the determination of the blood related parameters, the NIBP device 11, which is adapted to execute the above-described algorithms, may be seen as an entity of five operational modules or units, as is illustrated in FIG. 5. A control and timer unit 51 provided with the measurement timer 52 is configured to control the measurement by controlling a cuff drive unit 53, a data measurement unit 54, and a parameter determination unit 55. The control and timer unit is configured to supply inflate and deflate commands to the cuff drive unit and corresponding start and stop commands to the data measurement unit for starting and stopping the recording of the data. The control and timer unit may also receive quality information from the data measurement unit, thereby to be able to stop the measurement before the measurement timer expires. The control and timer unit may further control the determination of the blood pressure related parameters in the parameter determination unit 55. The figure further shows the pressure sensor 56 of the NIBP device, from which the data measurement unit 54 receives the pressure data when the cuff is pressurized to the target pressure.

As may be deduced from the description of FIGS. 1 and 5, a conventional NIBP device may be upgraded to enable the device to determine blood related parameters in the above-described manner. Such an upgrade may be implemented, for example, by delivering to the device a software module that enables the device to control the cuff pressure and process the data received from the cuff pressure sensor in the above-described manner. The software module is therefore configured to perform, when executed by the NIBP device, the operations corresponding to units 51, 52, 54, and 55 of FIG. 5, i.e. algorithm 15. The software module may be delivered, for example, on a data carrier, such as a CD or a memory card, or the through a telecommunications network.

In one embodiment of the method, the parameters are determined only when enough high quality pressure data is received before the measurement timer expires. Step 220 is thus omitted in this embodiment. The target pressure may also be defined in various ways and an optimal target pressure may be searched for in the beginning of the measurement. That is, the actual recording phase may be preceded by a "training period" during which an optimal target pressure is defined by monitoring the quality of the received data. The quality may be monitored similarly as in step 44, for example.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural or operational elements that do not differ from the literal language of the claims, or if they have structural or operational elements with insubstantial differences from the literal language of the claims.

The invention claimed is:

1. A method for non-invasively determining blood pressure related parameters of a subject, the method comprising:
   inflating a cuff attached to a subject to an initial target pressure, wherein the initial target pressure is such that normal blood pressure oscillation of the subject appears in an output signal of a pressure sensor monitoring a pressure of the cuff;
   acquiring the output signal of the pressure sensor in a non-invasive blood pressure (NIBP) device while the cuff is maintained substantially at the initial target pressure, thereby to obtain blood pressure waveform data for the subject, wherein the acquiring continues for at most a predetermined time period;
   determining whether respiratory modulation is present in the output signal by tracking amplitude extremes of pressure pulses in the blood pressure waveform data;
   adjusting the target pressure if respiratory modulation is not detected in the output signal of the pressure sensor;
   reacquiring the output signal in the NIBP device while the cuff is maintained substantially at the adjusted target pressure to obtain the blood pressure waveform data for the subject, wherein the target pressure is readjusted and the output signal is reacquired at the adjusted target pressure until respiratory modulation is detected in the output signal, wherein the reacquiring continues for at most the predetermined time period; and
   deriving the blood pressure related parameters in the NIBP device from the blood pressure waveform data obtained at the target pressure at which respiratory modulation is present.

2. The method according to claim 1, further comprising
   starting a measurement timer in the NIBP device to measure the predetermined time period; and
   stopping the acquiring when the measurement timer expires.

3. The method according to claim 2, further comprising performing a data quality analysis in the NIBP device, wherein the performing comprises identifying high quality waveform data from the blood pressure waveform data, and wherein the deriving includes deriving the blood pressure related parameters from the high quality waveform data.

4. The method according to claim 3, further comprising
   monitoring the amount of high quality waveform data that has been identified; and
   stopping the acquiring when the monitoring indicates that the high quality waveform data identified fulfils predetermined criteria for the deriving.

5. The method according to claim 4, further comprising detecting respiratory cycles of the subject, wherein the performing of the data analysis comprises analysing the output signal of the pressure sensor during several consecutive respiratory cycles.

6. The method according to claim 4, wherein the stopping comprises stopping the acquiring when the monitoring indicates that the high quality waveform data identified fulfils predetermined criteria, in which the predetermined criteria requires that the high quality waveform data identified originates from a predetermined number of respiratory cycles.

7. The method according to claim 3, further comprising generating feedback information comprising instructions on adjusting the target pressure, in which the generating is performed in response to stopping of the acquiring.

8. The method according to claim 1, further comprising defining the initial target pressure based on an initial blood pressure measurement, thereby to obtain information about current blood pressure of the subject.

9. An apparatus for non-invasively determining, blood pressure related parameters of a subject, the apparatus comprising:
   a cuff control unit configured to inflate a cuff attachable to a subject to a target pressure, wherein the target pressure is such that normal blood pressure oscillation of the subject appears in an output signal of a pressure sensor monitoring a pressure of the cuff;
   a measurement unit configured to acquire the output signal of the pressure sensor while the cuff is maintained substantially at the target pressure, thereby to obtain blood pressure waveform data for the subject, wherein the measurement unit is further configured to determine whether respiratory modulation is present in the output signal of the pressure sensor by tracking amplitude extremes of pressure pulses in the blood pressure waveform data, and wherein the cuff control unit is configured to adjust the target pressure if the measurement unit cannot detect respiratory modulation in the output signal of the pressure sensor, wherein the cuff control unit continues to adjust the target pressure and obtain the output signal at the adjusted target pressure until the measurement unit detects respiratory modulation in the output signal, wherein the blood pressure waveform data is recorded at the target pressure at which respiratory modulation is detected;
   a control and timer unit configured to enable the measurement unit to acquire the output signal of the pressure sensor for at most a predetermined time period; and a parameter determination unit configured to derive the blood pressure related parameters from the recorded blood pressure waveform data.

10. The apparatus according to claim 9, wherein the control and timer unit is configured to start a measurement timer to measure the predetermined time period and to stop operation of the measurement unit when the measurement timer expires.

11. The apparatus according to claim 10, wherein the measurement unit is further configured to identify high quality waveform data from the blood pressure waveform data, and wherein the parameter determination unit is further configured to derive the blood pressure related parameters from the high quality waveform data.

12. The apparatus according to claim 11, wherein
   the measurement unit is further configured to monitor the amount of high quality waveform data that has been identified; and
   the control and timer unit is configured to stop operation of the measurement unit when the measurement unit indicates that the high quality waveform data identified fulfils predetermined criteria.

13. The apparatus according to claim 12, wherein the measurement unit is further configured to detect respiratory cycles of the subject, and to analyze the output signal of the pressure sensor during several consecutive respiratory cycles.

14. The apparatus according to claim 11, further comprising a feedback information unit configured to generate feedback information comprising instructions on adjusting the target pressure.

* * * * *